United States Patent
Ritt et al.

(10) Patent No.: US 8,206,990 B2
(45) Date of Patent: Jun. 26, 2012

(54) METHODS AND KIT FOR ISOLATING NUCLEIC ACIDS

(75) Inventors: Christoph Ritt, Langenfeld (DE); Christoph Erbacher, Haan (DE); Patrick Baumhof, Dusslingen (DE)

(73) Assignee: Qiagen GmbH, Hilden (DE)

(*) Notice: Subject to any disclaimer, the term of this patent is extended or adjusted under 35 U.S.C. 154(b) by 0 days.

(21) Appl. No.: 12/439,396

(22) PCT Filed: Oct. 10, 2007

(86) PCT No.: PCT/EP2007/008826
§ 371 (c)(1),
(2), (4) Date: Oct. 15, 2009

(87) PCT Pub. No.: WO2008/043551
PCT Pub. Date: Apr. 17, 2008

(65) Prior Publication Data
US 2010/0056769 A1    Mar. 4, 2010

Related U.S. Application Data

(60) Provisional application No. 60/828,813, filed on Oct. 10, 2006.

(30) Foreign Application Priority Data

Oct. 10, 2006 (EP) .................................. 06021210

(51) Int. Cl.
*G01N 30/56* (2006.01)
(52) U.S. Cl. ........................ 436/94; 436/161; 436/178
(58) Field of Classification Search .................. None
See application file for complete search history.

(56) References Cited

U.S. PATENT DOCUMENTS

| | | | |
|---|---|---|---|
| 5,155,018 A | 10/1992 | Gillespie et al. | |
| 5,234,809 A | 8/1993 | Boom et al. | |
| 6,027,945 A | 2/2000 | Smith et al. | |
| 2002/0081619 A1 | 6/2002 | Bastian et al. | |
| 2003/0008320 A1 | 1/2003 | Baker | |
| 2006/0134717 A1 | 6/2006 | Tellier et al. | |

FOREIGN PATENT DOCUMENTS

| | | |
|---|---|---|
| EP | 1526176 A2 | 4/2005 |
| EP | 1146049 B1 | 8/2005 |
| EP | 0818461 B1 | 9/2005 |
| EP | 0389063 B2 | 10/2006 |
| WO | 02/46398 A2 | 6/2002 |
| WO | 03/020981 A1 | 3/2003 |
| WO | 03/084976 A1 | 10/2003 |
| WO | 03/091452 A1 | 11/2003 |
| WO | 2005/045030 A1 | 5/2005 |
| WO | 2007015243 | 2/2007 |
| WO | 2008073175 | 6/2008 |

OTHER PUBLICATIONS

Abudiab,. Thaer et al. "Preparation of magnetic immobilized metal affinity separation media and its use in the isolation of proteins." Journal of Chromatography A (1998) 795 211-217.*
Anspach, Friedrich Birger. "Silica-based metal chelate affinity sorbents I. Preparation and characterization of iminodiacetic acid affinity sorbents prepared via different immobilization techniques." Journal of Chromatography A (1994) 672 35-49.*
Potty, Ajish S. R. et al. "Neutral additives enhance the metal-chelate affinity adsorption of nucleic acids: Role of water activity." Journal of Chromatography A (2006) 1115 88-92.*
Vockley, Jerry et al. "Purification of human adult and foetal intestinal alkaline phosphatases by monoclonal antibody immunoaffinity chromatography." Biochemical Journal (1984) 217 535-541.*
Benzanilla, Magdalena et al. "Adsorption of DNA to Mica, Silylated Mica, and Minerals: Characterization by Atomic Force Microscopy." Langmuir (1995) 11 655-659.*
Solberg, Sean M. et al. "Adsorption of DNA into Mesoporous Silica." Journal of Physical Chemistry B (2006) 110 15261-15268.*
Murphy, Jason C. et al.: "Nucleic Acid Separations Utilizing Immobilized Metal Affinity Chromatography", Biotechnology, Butterworths, London, GB, vol. 19, No. 3, May 20, 2003, pp. 982-986.
Balan, Sindhu et al.: "Metal Chelate Affinity Perception of RNA and Purification of Plasmid DNA", Biotechnology Letters, vol. 25, No. 13, Jul. 2003, pp. 1111-1116.
Ihara, Toshihiro et al.: "DNA Separation Using ZR (IV)-loaded Resin Through Ligand Exchange", Analytical sciences, vol. 17, No. SUPPL, 2001, pp. IL229-IL231.
International Search Report for PCT/EP2007/008826 dated Jan. 31, 2008.
Written Opinion of the International Searching Authority for PCT/EP2007/008826 dated Jan. 31, 2008.
Office Action for European Patent Application 07818897.6, Dated Mar. 14, 2011.

* cited by examiner

*Primary Examiner* — Yelena G Gakh
*Assistant Examiner* — Christopher A Hixson
(74) *Attorney, Agent, or Firm* — Baker Donelson Bearman Caldwell & Berkowitz P.C.

(57) ABSTRACT

The present invention is related to a method for isolating a target nucleic acid from a sample comprising said target nucleic acid, comprising the steps of mixing a sample containing said target nucleic acid with a binding solution and a nucleic acid binding matrix, binding at least part of said target nucleic acid to said nucleic acid binding matrix, wherein said nucleic acid binding matrix is treated simultaneously or has been previously treated with at least one compound comprising a metal substance selected from the group consisting of metals of the main groups 13 to 16, semimetals and transition metals for reducing non-target nucleic acid contaminations or wherein said nucleic acid binding matrix is modified with hydrophobic groups. Furthermore, respective kits and reagents are provided with the teaching of the present invention.

23 Claims, 3 Drawing Sheets

METHODS AND KIT FOR ISOLATING NUCLEIC ACIDS

CROSS REFERENCE TO RELATED APPLICATIONS

This application is a §371 National Stage Application of PCT/EP07/08826 filed Oct. 10, 2007, which claims priority from U.S. Provisional Application No. 60/828,813, filed Oct. 10, 2006, and European Patent Application No. 06021210.7, filed Oct. 10, 2006.

FIELD OF THE INVENTION

It is the object of the present invention to provide an improved method for isolating/purifying target nucleic acids from a sample. It is also the aim of the present invention to provide a respective nucleic acid isolation/purification kit and nucleic acid binding matrixes.

BACKGROUND OF THE INVENTION

Methods for isolating and preparing nucleic acids, both RNA and DNA, are used since several years in the state of the art and increasingly gain importance. Several purification methods are known, such as extraction/precipitation, chromatography, in particular adsorption chromatography, electrophoresis and affinity separation.

The known methods usually involve lysing the biological material by mechanical action and/or chemical action and/or biological action e.g. by treating the material with a detergent in the presence of protein degrading enzymes. Several different methods are also known for recovery of the nucleic acids after lysis. Some involve several extractions with organic solvents, for example with phenol and/or chloroform. These standard methods for isolating nucleic acids are very laborious and time-consuming. The relatively large number of steps required to purify nucleic acids from the starting materials also increase the risk of contaminations, especially with non-target nucleic acids.

Particularly useful are methods which are based on the non-sequence specific adsorption of the nucleic acids to the binding matrixes such as silica matrixes. Improved methods for isolating nucleic acids include the use of chaotropic salts, for example guanidinium chloride, and/or the use of alcohols, for example ethanol or isopropanol (see e.g. U.S. Pat. No. 5,234,809 and EP 1 146 049).

EP 0 389 063 also pertains to a process for isolating nucleic acids. The source containing the nucleic acids is lysed in the presence of chaotropic ions and then treated with a material which will adsorb nucleic acids, such as diatomaceous earth or other silica-containing mineral supports which are commonly used for nucleic acid isolations.

U.S. Pat. No. 5,155,018 discloses a process for isolation and purification of biologically active RNA from biological sources containing RNA, DNA and other cell contents. The source containing RNA is contacted with particles which consist of silica containing materials, such as finely dispersed glass. The binding buffer from which the RNA is adsorbed to the material comprises acidified solutions containing chaotropic salts. Under such conditions, RNA is specifically bound to the silica material.

WO 2005/045030 discloses an isolation and purification technology also incorporating the use of a porous matrix consisting of a material based on silica or of a silica coated material, which binds nucleic acids. However, the described method is performed in the absence of a chaotropic salts and alcohols.

The raw preparation of target nucleic acids is usually performed in order to enable subsequent analysis reactions. These subsequent reactions impose certain demands on both the isolation procedure and the purity and integrity of the isolated target nucleic acids. Especially when followed by enzymatic amplification reactions, such as PCR (polymerase chain reaction), LCR (ligase chain reaction), NASBA (nucleic acid sequence-based amplification), or SSR (self-sustained sequence replication), the preparation of the target nucleic acids should be free of contaminants such as cell components and especially non-target nucleic acids in order to avoid false results.

Genomic DNA (gDNA) is a common contaminant of RNA isolations. Consequently, some commercially available RNA isolation kits provide a protocol for selective enzymatic removal of contaminating gDNA with deoxyribonuclease I (DNase I). However, treatment with DNase I occasionally results in a reduction of RNA yield and degradation of RNA by ribonucleases (RNases) that can contaminate commercially produced DNase I. Besides that, DNase I treatment adds hands-on time, extends the length of time required for the process, requires the addition of metal ions which can interfere with downstream processes and furthermore, it increases the overall costs of the RNA isolation.

Thus, it was attempted to improve the purity of the nucleic acid preparations, especially RNA preparations, wherein it was aimed to keep the content of contaminations such as genomic DNA as low as possible.

EP 0 818 461 e.g. discloses the use of lithium salts in the chaotropic lysis solution under certain conditions in order to increase the yield of pure RNA and in order to reduce genomic DNA contaminations. However, the obtained results are not satisfying.

EP 1 526 176 teaches the use of a pre-filtration technology in order to remove the genomic DNA from the RNA fraction. The method is based on the known RNA technology using chaotropic salts and a silica matrix for adsorbing the RNA. However, before the RNA is adsorbed at the silica matrix for isolation, the lysate is applied to a pre-filtration column in order to remove the DNA. During passage of the homogenate through the pre-filtration column, cellular contaminants, including genomic DNA, remain within the pre-filtration column while the effluent contains partially purified RNA. This RNA is then further purified by applying the effluent onto a second filtration column for adsorbing and washing the RNA. The drawback of this method is obvious, as two columns are necessary for purification which increases the hands-on time and costs.

BRIEF SUMMARY OF THE INVENTION

It is the object of the present invention to provide an improved method for isolating/purifying target nucleic acids from a sample. It is also the aim of the present invention to provide a respective nucleic acid isolation/purification kit and nucleic acid binding matrixes.

DETAILED DESCRIPTION OF THE INVENTION

Figure 1:
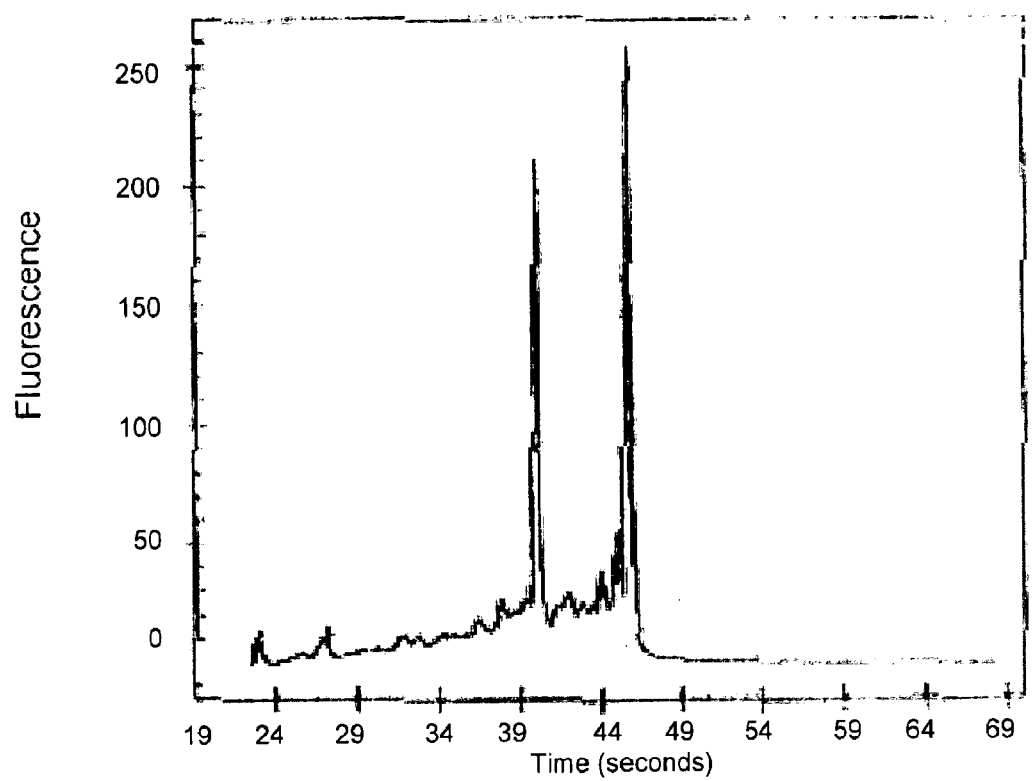
FIG. 1 shows a profile of an eluate of a titanium (IV) chloride pre-treated column analysed on an Agilent 2100 Bioanalyzer as described in Example 1.

According to a first aspect, the present invention solves this object by providing a method for isolating a target nucleic acid from a sample comprising at least said target nucleic acid, comprising the steps of contacting said sample containing said target nucleic acid with a nucleic acid binding matrix and binding at least part of said target nucleic acid to said nucleic acid binding matrix, wherein said nucleic acid binding matrix is or has been treated in order to alter the binding properties of the nucleic acid binding matrix in order to reduce binding of contaminants to said nucleic acid binding matrix.

According to a first embodiment, said nucleic acid binding matrix is treated simultaneously (during contacting/binding of the target nucleic acid) or has been previously treated with at least one compound comprising a metal substance selected from the group consisting of metals of the main groups 13 to 16, semimetals and transition metals in order to reduce non-target nucleic acid contaminations in the obtained target nucleic acid. The target nucleic acid is then obtained from the nucleic binding matrix by using known procedures such as e.g. an elution process.

It was surprisingly found by the inventors that the treatment of the nucleic acid binding matrix with at least one compound comprising a metal substance selected from the group consisting of metals of the main groups 13 to 16, semimetals and transition metals considerably decreases the amount of non-target nucleic acids contaminations found in the isolated target nucleic acid probe. For example, the amount of genomic DNA contaminations in a RNA preparation can be reduced by up to 60 fold when using the technology according to the present invention.

According to a second embodiment, said nucleic acid binding matrix carries/is provided with hydrophobic groups in order to reduce binding of contaminants, in particular genomic DNA in case of a RNA preparation. It was surprisingly found that providing hydrophobic groups on the nucleic acid binding matrix surface has a similar advantageous effect as the treatment with metal compounds. Said hydrophobic groups may be attached covalently or non-covalently to the nucleic acid binding matrix.

The method according to the present invention is especially suitable for the isolation/purification of RNA from a sample. The RNA may be of any kind and size. The isolation of RNA having less genomic DNA contaminations is especially desirable as genomic DNA is fairly stable compared to RNA thus requiring harsh methods for removal (see e.g. above). However, by treating or derivatizing the nucleic acid binding matrix with said binding properties altering compound according to the present invention (see the alternatives described above), the amount of genomic DNA contaminations is considerably decreased when using standard protocols of RNA isolation/purification known in the state of the art. The remarkable effect on the purity of the obtained RNA renders the above described additional treatments (e.g. DNase treatments) for many applications obsolete. It is also not necessary to use several columns/matrixes but a one column/matrix procedure can be used. The special treatment of the nucleic acid binding matrix as taught by the present invention thus considerably improves the standard methods for nucleic acid and especially RNA isolation and purification as contaminations, especially with non-target nucleic acids, are avoided. The obtained depletion of genomic DNA contaminants in case of a RNA preparation is e.g. at least 2 fold, but is usually even greater and is e.g. at least 4 fold, 6 fold, 10 fold, 12 fold, 14 fold, 20 fold or even higher such as 30, 50 or even more than 60 fold according to some embodiments (please refer e.g. to example 5).

The nucleic acid is preferably bound by adsorption and thus differs from ion exchange chromatography or affinity based purification methods. The binding properties altering compound according to the present invention which has the effect that contaminations of the obtained target nucleic acid preparation are reduced, comprises according to the first embodiment a metal substance selected from the group consisting of metals of the main groups 13 to 16, semimetals and transition metals. Said compound is not selected from alkaline metal or alkaline earth metal substances such as lithium, potassium and magnesium. Accordingly, said definition does thus not comprise compounds such as e.g. NaCl, $MgCl_2$ and $CaCl_2$.

The binding properties altering compound of the present invention may be used in form of a solid matter. However, it may also be used/be present in dissociated or solvated form and thus in a solution. In case the compound is not a salt itself, which is preferred according to certain embodiments, then the compound may also be present in form of a salt. It should be understood that the compound which is used in order to treat the nucleic acid binding matrix comprises a metal as defined above is not present in its elemental form but, depending on the kind of compound (e.g. a salt or a hydrolysable compound) and the comprised metal, in different oxidation states. However, it should be understood that it also lies within the scope of the present invention to produce the binding properties altering compound in situ e.g. by using appropriate reducing agents in order to generate metals of the appropriate oxidation state from elemental metal(s) for obtaining the actual compound (usually in its dissociated form).

Metals of the main groups 13 to 16 are Al, Ga, In, Sn, Tl, Pb, Bi and Po. Sn and Al are very suitable metal substances of this group to be used as compound constituents for altering the binding properties of a nucleic acid matrix. However, Sn is most preferred. The metals of the main groups 13 to 16 may also be selected from the group consisting of Ga, In, Sn, Tl and Po.

Classical semimetals are for example B, Si, Ge, As, Sb and Te. B and Ge are especially suitable semimetal substances for altering the binding properties of a nucleic acid matrix in order to reduce non-target nucleic acid contaminations.

Classical transition metals are e.g. Sc, Ti, V, Cr, Mn, Fe, Co, Ni, Cu, Zn, Y, Zr, Nb, Mo, Ru, Rh, Pd, Ag, Cd, La, Hf, Ta, W, Re, Os, Ir, Pt, Au, Hg. The transition metal may be selected from the group consisting of Ti, V, Cr, Mn, Fe, Ni, Cu, Zn, Zr, Nb, Mo, Pd, Ag, Cd, Ta, W, Os, Pt, Au, Hg or may be selected from the group consisting of Ti, V, Cr, Fe, Ni, Cu, Zn, Zr, Mo, Pd, Ag, Cd, Ta, W and Os. Fe, Zr, Ta and Ti are especially suitable transition metal substances.

These compounds comprising metal substances selected from the group consisting of metals of the main groups 13 to 16, semimetals and transition metals suitable for altering the binding properties of a nucleic acid binding matrix are preferably used in form of a salt, a salt complex or as a hydrolysable compound such as an alkoxide or as an amide, an alkylene or an hydride. Suitable anions of the metals of the main groups 13 to 16, semimetals and transition metals which can be used according to the present invention are for example halogenides, pseudohalogenides, nitrates, phosphates and sulphates. Halogenides such as chlorides, bromides and iodides are especially preferred. Furthermore, also the conjugated bases of organic acids such as acetates, citrates and tartrates are suitable.

Suitable compounds which can be used according to teachings of the present invention are inter alia zirconium chloride, titanium (IV) chloride, aluminium chloride, stannous chloride, ferrous (II) chloride, ferric (III) chloride, aluminium isopropoxide, titanium isopropoxide, zirconium isopropoxide, chlorotriisopropyl orthotitanate, triisopropylborate, zirconium isopropoxide isopropanol-complex, zirconium oxide chloride, aluminium triisopropylate and tantalum pentachloride.

In order to alter the binding properties of the nucleic acid binding matrix in order to avoid contaminations in general and especially of non-target nucleic acids, it is e.g. only necessary to contact the nucleic acid binding matrix with said binding properties altering compounds according to one embodiment of the present invention. According to a different embodiment, said nucleic acid binding matrix is at least partially modified with hydrophobic groups and hence carries hydrophobic groups on its surface which is in contact with the target nucleic acid.

A respectively treated/modified nucleic acid binding matrix is then ready for isolating the target nucleic acid from a sample comprising usually at least two different kinds of nucleic acids, wherein non-target contaminations are reduced in the isolated target specimen.

As indicated above, there are several suitable methods for treating the nucleic acid binding matrix in order to improve the binding specificity towards the target nucleic acid (especially RNA).

According to one embodiment, the nucleic acid binding matrix is contacted with said binding properties altering compound by immersing said nucleic acid binding matrix in a solution containing said compound comprising a metal substance selected from the group consisting of metals of the main groups 13 to 16, semimetals and transition metals. In such a solution the compound is usually present in its dissociated form. After immersion and optionally removal of the solvent and drying of the nucleic acid binding matrix, said respectively treated nucleic acid binding matrix is ready for use. Said pre-treatment enhances the binding selectivity of the nucleic acid binding matrix towards the target nucleic acid (preferably RNA) as e.g. less non-target nucleic acids (such as genomic DNA) are bound. It is believed that this is due to chemisorption and/or physisorption processes between the compound (or a compound constituent) and the matrix. This method has the advantage that the altered nucleic acid binding matrix having improved properties can be directly included in the standard nucleic acid isolation protocols/kits used in the state of the art. The pre-treatment can be performed by the provider/manufacturer of a respective kit or by the manufacturer of the nucleic acid binding matrix, respectively. This procedure has the advantage that the customer is not confronted with a new protocol but can stick to the known nucleic acid isolation procedures. This method is especially suitable if the nucleic acid binding matrix is to be treated with hydrolysable metal compounds such as for example metal halogenides or metal alkoxides which may be used in an aprotic, anhydrous solvent such as for example THF. Preferred substances for this treatment method are zirconium, titanium, tantalum, aluminium and boron. But also metal salts such as the already mentioned metal halogenides, metal nitrates, phosphates and sulphates are suitable for this treatment method in order altering the binding properties of the nucleic acid binding matrix. These compounds may be used for pre-treatment in a protic or in an aprotic solvent. Preferred metals are non-ferrous metals (Buntmetalle) including aluminium, germanium and tin.

Said immersion solution comprises said compound comprising a metal substance selected from the group consisting of metals of the main groups 13 to 16, semimetals and transition metals preferably in a concentration of at least 0.05%, preferably at least 0.1%. Good results can be obtained with an immersing solution comprising said compound in a concentration ranging from approximately 0.05 to 20%, 0.1 to 15% or 0.1% to 10%. Higher concentrations are of course also possible and thus comprised by the scope of the present invention but not necessary in order to achieve good results.

According to a further embodiment the nucleic acid binding matrix is contacted with said binding properties altering compound according to the present invention in the gas phase wherein vapours of the compounds are responsible for altering the binding properties of the matrix.

According to a different embodiment said binding properties altering compound is added to a liquid solution which is applied to the nucleic acid binding matrix during the target nucleic acid isolation protocol:

Said solution comprising said binding properties altering compound according to the present invention may be predominantly designed for pre-treating said nucleic acid binding matrix directly prior to performing the nucleic acid isolation. Thus before applying the sample comprising the target nucleic acid to be isolated to the nucleic acid adsorption matrix, the matrix is pre-treated with the pre-treatment solution, thereby altering and respectively improving the binding properties of the nucleic acid binding matrix such that less non-target nucleic acid contaminations are present in the target nucleic acid isolation. The compound is usually present in said solution in its dissociated form. Such a pre-treatment solution may be, e.g., a component of a nucleic acid isolation kit. Said pre-treatment solution comprises said compound preferably in a concentration of at least 0.05%, preferably of at least 0.1%. Also higher concentrations such as 1%, 5% 10% or more may be used. However, good results can be obtained with solutions having a concentration of approximately 0.05 to 15%, 0.1 to 10%, 0.1 to 5% or 0.1 to 2.5 or 0.1 to 1.5%. A protic or aprotic solvent may be used. In order to facilitate a thorough contact of said pre-treatment solution with said nucleic acid binding matrix and an easy removal thereof after treatment, said matrix may be centrifuged or vacuum may be applied.

Alternatively, said compound comprising a metal substance selected from the group consisting of metals of the main groups 13 to 16, semimetals and transition metals may be added to the lysis and/or binding buffer usually used for isolating the target nucleic acid. This method has again the advantage that the standard protocol used for nucleic acid isolation may remain unaltered what is convenient for the customer/user. According to one embodiment, said compound comprising a metal substance selected from the group consisting of metals of the main groups 13 to 16, semimetals and transition metals is included in the lysis and/or binding buffer comprising a chaotropic agent. A chaotropic agent generally comprises a chaotropic ion provided at a concentration sufficiently high to cause the nucleic acid to loose its secondary structure. Chaotropes are thought to disrupt hydrogen-bonding in water. Typical chaotropic agents comprise a guanidinium salt, urea, or an iodide, chlorate, perchlorate or (iso)thiocyanate. Preferred chaotropic agents include guanidinium thiocyanate and guanidinium hydrochloride. In case said compound comprising a metal substance selected from the group consisting of metals of the main groups 13 to 16, semimetals and transition metals is added to a solution comprising a chaotropic salt, said compound altering the binding properties of said nucleic acid binding matrix is preferably no chaotropic salt itself. Said compound is preferably present in the lysis and/or binding buffer in a concentration of at least 0.05 mM. Very suitable concentrations range from approximately 1 mM to 10 or 20 mM.

These methods (direct pre-treatment solution, altered buffer) have the advantage that they are very quick as no long immersion process or the like is needed for achieving the beneficial results. These treatment methods are especially preferred for stannous and ferric or ferrous compounds which are preferably used as salts such as e.g. stannous chloride or ferric or ferrous chloride.

It is also within the scope of the present invention to use more than one of the described methods in order to treat the nucleic acid binding matrix. It is also possible to use more than one compound (e.g. 2, 3 or 4 compounds) for each treatment. The inventors found that a combination treatment leads to considerable synergistic effects as such a procedure even further improves the purity of the isolated target nucleic acid as contaminations, especially non-target contaminations, such as DNA in case of a RNA preparation are further reduced.

Thus according to one embodiment, the nucleic acid binding matrix is immersed in a solution comprising at least one compound comprising a metal substance selected from the group consisting of metals of the main groups 13 to 16, semimetals and transition metals. The matrix is then optionally freed from solvent and dried. Such a pre-treated nucleic acid binding matrix is then used for target nucleic acid isolation or as a respective component for a kit. In order to further reduce the risk of contaminations, the method or the respective kit provides a solution which comprises a compound comprising a metal substance selected from the group consisting of metals of the main groups 13 to 16, semimetals and transition metals for further altering the binding properties of the nucleic acid binding matrix. Said compound may be for example comprised in a separate buffer or may be comprised in the lysis and/or binding buffer.

According to the second alternative of the present invention, the nucleic acid binding matrix carries hydrophobic groups in order to obtain a target nucleic acid preparation, preferably RNA, with a reduced amount of non-target nucleic acid contaminations, in particular genomic DNA. Hence, the same result is achieved by this alternative embodiment as with the metal compound alternative described above, in order to solve the problem underlying the present invention.

The hydrophobic groups can be coupled covalently or non-covalently to the nucleic acid binding matrix. Covalent coupling can e.g. occur via appropriate linkers.

Said hydrophobic group is preferably a substituted or unsubstituted alkyl substituent having a length of between 1 to 50, preferably 1 to 40, more preferably 1 to 20 C-atoms. Said alkyl substituent may have a branched or linear structure. Said alkyl substituent may carry a functional group, e.g. one comprising O, S, N, halogens or phosphor groups such as e.g. alcohols, ether, ester, amides, amines, nitriles or similar functional groups.

According to one embodiment, said nucleic acid binding matrix is derivatised with a silane compound carrying at least one hydrophobic group. Said silane compound is preferably a reactive silane compound and may carry a functional group. Silane compounds basically may incorporate the same functional groups as alkanes. Said silane compound carrying at least one hydrophobic group can be selected from the group consisting of alkoxysilanes and aminosilanes, halosilanes. Said silane compound may be mono, bi or trifunctional.

Depending on the type of silane compound used the attachment of the hydrophobic groups/hydrophobic coating may vary. Monofunctional silane compounds e.g. may be coupled in form of a monolayer which is covalently coupled to the nucleic acid binding matrix. In case of di- or trifunctional silane compounds it is assumed that a three-dimensional layer/coating is formed on the nucleic acid binding matrix. Said layer is not necessarily covalently attached to the underlying nucleic acid binding matrix. However, covalent links are formed within said layer/coating. Said three-dimensional layer may cover the nucleic acid binding matrix partially or completely. In case the nucleic acid binding matrix is basically completely covered with said three-dimensional layer, predominantly said new layer comes in contact with the nucleic acid molecules to be isolated. Hence, a silica proportion is provided by said silane compound which may adsorb the nucleic acids.

According to one embodiment said silicon-containing nucleic acid binding matrix is derivatised with hydrophobic groups by contacting said matrix with a compound selected from the following group of compounds:

$R^1R^2R^3Si\text{—}OR^4$

$R^1R^2Si(OR^3)\text{—}OR^4$

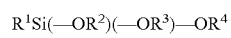

$R^1Si(\text{—}OR^2)(\text{—}OR^3)\text{—}OR^4$ wherein $R^1R^2R^3$ and/or $R^4$ have the same or a different meaning and are independently selected from the group consisting of hydrogen, alkyl substituent, alkylene substituent or a functional group and wherein at least at least one of $R^1$, $R^2$ or $R^3$ and/or $R^4$ is an alkyl substituent which may be substituted or unsubstituted. The alkyl substituent of the alkoxy group (OR) may have a length of between 1 to 20, preferably 1 to 9 C-atoms and may have a linear or branched structure. Preferably, said alkyl substituent is a short alkyl substituent of 1 to 5, preferably 1 to 3 C atoms. Preferably said alkoxy group is a methoxy or an ethoxy group. The silane compound may carry several identical alkoxy groups such as e.g. $R^1Si(OR^2)_3$.

The alkyl substituent/s which is/are not present in the alkoxy group preferably has/have a longer length than the alkyl group comprised in the alkoxy group. Said alkyl substituent may have a length between 1 to 40 C-atoms. Said alkyl group may also be linear or branched. Preferably it has a length of 1 to 25, most preferably 1 to 20 C-atoms and does not carry functional groups.

Reactive halosilanes carrying at least one hydrophobic group such as an alkyl group as described above may comprise a chloro or bromo group as functional group.

Suitable aminosilanes carry at least one hydrophobic group may carry an alkyl group as described above. They may be selected from the following groups of compounds:

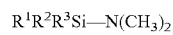

$R^1R^2R^3Si\text{—}N(CH_3)_2$

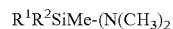

$R^1R^2SiMe\text{-}(N(CH_3)_2$

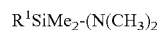

$R^1SiMe_2\text{-}(N(CH_3)_2$ wherein $R^1R^2R^3$ have the same meaning as defined above.

According to one embodiment, said matrix is contacted with a silane compound selected from the group consisting of:

propyltriethoxysilane (PTS), octadecyltrimethoxysilane (OTM), hexadecyl-trimethoxysilane (HMS), octyltrimethoxysilane (OTS) and tetradecyltrimethoxysilane and octadecyltrimethoxysilane.

Said hydrophobic groups can be applied to the silicon-containing nucleic acid binding matrix via several methods which are known in the state of the art. Non-limiting examples are e.g. immersion in appropriate compounds (see above), acidic hydrolysis, applying a polymeric coating, plasma coating grafting onto polymerisation or other suitable methods.

According to one embodiment, said alternative treatment methods for altering the binding properties of the nucleic acid binding matrix in order to reduce non-target nucleic acid contaminations may be used in combination. As can be seen from the examples, an additive effect can be observed.

As outlined above, the method described herein is especially suitable for isolating RNA from a sample, wherein the amount of genomic DNA contaminations is reduced.

The nucleic acid binding matrix which can be used according to the present invention may be of any kind which is suitable for performing a respective nucleic acid isolation/purification. It is preferred that the surface of the nucleic acid binding matrix which is in contact with the target nucleic acid comprises silicon in order to enhance nucleic acid binding. Depending on the embodiment used, there are several embodiments to obtain a respective silicon-containing surface. E.g. said nucleic acid binding matrix may include a mineral or a polymer. A mineral matrix preferably consists of porous or non-porous metal oxides or mixed metal oxides, particularly silica gel, silica particles or materials predominantly consisting of glass, such as unmodified glass particles, powdered glass, quartz, alumina, zeolites, titanium, and zirconium dioxide. Said porous or non-porous matrix may be present in the form of loose packings or may be embodied in the form of filter layers e.g. made of glass, quartz or ceramics, and/or a membrane in which e.g. silica gel is arranged, and/or of particles or fibers made of mineral supports and fabrics of quartz or glass wool, as well as latex particles with or without functional groups, or frit materials made of polyethylene, polypropylene, polyvinylidene fluoride, especially ultra high molecular weight polyethylenen and high density polyethylene. In some embodiments, the matrix is or comprises polyacrylate, polystyrene, latex, polyacrylonitrile, polyvinylchloride, methacrylate, and/or methyl methacrylate. A membrane suitable for RNA isolation may also be selected from the group consisting of BTS, PVDF, nylon, nitrocellulose, polysulfone, MMM, PVP, and composites thereof as it is described e.g. in EP 1 526 176. According to a further embodiment, a silica surface is provided by an appropriate coating, e.g. a silane coating as described above.

Common and thus suitable forms of the nucleic binding matrix include, but are not limited to, beads, magnetic particles, columns, membranes and filters.

It is preferred, that the matrix material includes a mineral such as a silica-based matrix. Hence, according to one embodiment a silica-containing nucleic acid binding matrix is used. Silica may constitute part of the matrix carrier or can be comprised in a surface coating. Respective matrices are capable of reversibly binding nucleic acids. It is believed that said binding occurs via adsorption as well as precipitation reactions. DNA apparently binds better to a respective silica-containing nucleic acid binding matrix than RNA. Without being bound by this theory, it is assumed that the treatments performed according to the teachings of the present invention in fact lower binding of DNA to the matrix. RNA binding, which occurs often via a precipitation reaction is basically not affected by said treatment. Hence, in case of a RNA preparation, less contaminating genomic DNA is present in the RNA preparation.

Very often porous silica membranes are used in the state of the art for isolating nucleic acids which is thus also preferred. Such membranes are especially suitable for isolating RNA. According to one embodiment, said porous matrix material is a membrane embedded in a single column filter tube or is integrated in a multi-well filter plate, preferably a 96-well filter plate or a 384-well filter plate. The lysate—or in case of a centrifugation step the supernatant of the centrifuged lysate—is filtered by moving the lysate through the porous matrix material, for example by centrifugation or by applying a vacuum or the like. During the passage, the target nucleic acid is bound to said nucleic acid binding matrix.

According to a preferred embodiment said nucleic acid binding matrix has magnetic properties and is accordingly magnetically attractable. Respective magnetic particles are commonly used because they can be easily processed by using a magnet. The magnetic properties can be provided by using magnetic metal oxide, such as iron oxide. Preferably, said magnetic material such as iron oxide forms a core wherein the siliceous material covers the magnetic core. Said core may have ferri-, ferro- or superparamagnetic properties. The RNA isolation properties of respective magnetic silica particles can be greatly improved, if these particles are treated with a compound comprising a substance selected from the group consisting of metals of the main groups 13 to 16, semimetals and transition metals as described above. Respectively treated magnetic particles are preferably used in automated RNA isolation protocols, wherein the number of steps necessary for obtaining purified RNA is supposed to be reduced. As described above, the present invention makes additional steps such as e.g. DNase treatments obsolete, even though they can be performed if desired.

According to one embodiment the nucleic acid isolation method according to the present invention comprises the following basic steps:

The sample comprising the target nucleic acid is lysed e.g. by using a lysis buffer, mechanical lysis, physical lysis or biological lysis by using appropriate enzymes if necessary. Preferably, the sample is disrupted in the presence of a lysis buffer. Afterwards, a complex of target nucleic acid (e.g. RNA) and preferably a silica based matrix is formed upon binding of the target nucleic acid to the nucleic acid binding matrix. Due to the special treatment of the nucleic acid binding matrix e.g. with a compound comprising a substance selected from the group consisting of metals of the main groups 13 to 16, semimetals and transition metals, or by derivatizing said nucleic acid binding matrix with hydrophobic groups, the target nucleic acid (e.g. RNA) is isolated with a higher purity compared to non-treated nucleic acid binding matrices, meaning that the obtained target nucleic acid sample contains less contaminations with non-target nucleic acids (particularly genomic DNA). Please note that even though generally desirable, it is not necessary in the context of the present invention that binding to the target nucleic acid is improved by said treatment. In order to obtain said described beneficial results regarding the reduced non-target nucleic acid contaminations it would be e.g. already sufficient if the binding of the nucleic acid binding matrix to contaminants such as non-target nucleic acids (e.g. genomic DNA) is reduced compared to untreated matrices. This would already reduce the risk that non-target nucleic acids are bound by the nucleic acid binding matrix and thus eluted together with the target nucleic acid as contaminants. Said mechanism—reducing the affinity of the matrix to non-target nucleic acids—is especially suitable for avoiding genomic DNA contaminations as DNA often has a higher affinity especially towards silica based matrices than RNA (see above).

If used, the lysis buffer mixture is usually removed from the resulting complex of target nucleic acid (e.g. RNA) and nucleic acid binding matrix. Afterwards, the complex is preferably washed and the target nucleic acid (RNA) is obtained, e.g. eluted.

As outlined above, the present invention describes a remarkable improvement of standard nucleic acid and especially RNA isolation protocols by improving the purity of the obtained target nucleic acids (especially RNA) by lowering the content of non-target nucleic acid contaminants (particularly genomic DNA). This is achieved according to one embodiment by treating the nucleic acid binding matrix with a compound comprising a metal substance selected from the group consisting of metals of the main groups 13 to 16, semimetals and transition metals. Alternatively, the nucleic acid binding matrix is derivatised with hydrophobic groups.

The method described herein can be used for selectively isolating any kind of target nucleic acid. Which target nucleic acid will be bound by the nucleic acid binding matrix (e.g. RNA or DNA) usually depends on the chosen binding/buffer conditions which should be adjusted accordingly. The nucleic acid to be isolated may thus be DNA, RNA or a modified form thereof of any size. Where the nucleic acid is DNA, this may be ds or ss. Where the nucleic acid is RNA, this may be any RNA of any size such as e.g. or total RNA, rRNA, mRNA, small RNAs such as miRNAs and siRNA. As the essence of the invention lies in said treatment/alteration of the nucleic acid binding matrix it is not necessary to refer in detail to defined protocols for nucleic acid isolation employing the use of a nucleic acid binding matrix, as these protocols are numerable and also well known and widely used in the state of the art. All these known standard methods for nucleic acid and especially RNA isolation can be used in the context of the present invention (please refer e.g. to US 2002/0081619, EP1 146 049, WO 03/084976, WO 03/091452, U.S. Pat. No. 6,027,945, citing further references, all herein incorporated by reference). Subsequently, some general aspects of standard methods suitable for use in the context of the present invention are subsequently discussed for information purposes.

Preferably, samples containing the target nucleic acids are first lysed. When extracting the target nucleic acid from cells it is preferred to use an aqueous lysis system containing chaotropic substances and/or other salts by, in the simplest case, adding them to the cells. Optionally, the lysis process may be promoted by mechanical action. Systems for lysing the sources containing the nucleic acids are preferably solutions of chaotropic substances in concentrations of from 0.1 to about 10 M. As said chaotropic substances, there may be used, in particular, salts, such as sodium perchlorate, guanidinium chloride, guanidinium isothiocyanate/guanidinium thiocyanate, sodium iodide, potassium iodide, and/or combinations thereof. For RNA isolation it was found as a good mode of operation that as lysis buffers and/or binding buffers, there may be used in particular, aqueous solutions containing from 0.5 to 8 M of guanidinium isothiocyanate/guanidinium thiocyanate, and/or guanidinium chloride, and from 0 to 50% of ethanol and/or isopropanol.

Since nucleic acids will generally bind well to mineral supports, for example, in sodium chloride/ethanol mixtures and can be eluted under conditions of low ionic strength or with water, it may be supposed that the salt solutions used in the process according to the invention need not necessarily contain chaotropic salts (which are anyhow preferred ingredients though), but that any salt solution in combination with a material containing alcohol groups may be used according to certain embodiments (please refer e.g. to the method described in US 2002/0081619 herein incorporated by reference).

Aqueous solutions containing salts, such as sodium chloride, lithium chloride, potassium chloride, sodium acetate, magnesium chloride, in concentrations of from 0.1 to 10 M, or urea in corresponding concentrations of from 0.1 to 10 M, and/or combinations of such materials may also be used as aqueous systems for lysing or binding the sources containing the nucleic acids.

The materials containing the alcohol groups are preferably lower aliphatic alcohols comprising from 1 to 5 carbon atoms, such as methanol, ethanol, isopropanol, butanol and pentanol. They are preferably employed in concentrations of from 1 to 90% per volume.

Optionally, washing steps may be performed prior to the elution of the respective target nucleic acids (single stranded nucleic acids or double stranded nucleic acids).

As the solution for washing out or eluting nucleic acids bound to the matrix which is preferably a mineral support such a silica-based matrix, there may be used an aqueous solution containing from 0.1 to 3 M of guanidinium isothiocyanate/guanidinium thiocyanate, and/or guanidinium chloride, together with from 1 to 30% of ethanol and/or isopropanol.

The sample containing said nucleic acids to be separated from each other (RNA from DNA) is usually contacted with at least one nucleic acid binding matrix, wherein the treatment conditions are adjusted with an appropriate aqueous mixture of salts, especially chaotropic substances, and according to a preferred embodiment materials containing alcohol groups, such that the single stranded nucleic acid fraction containing RNA is predominantly adsorbed by the nucleic acid binding matrix whereas the double stranded nucleic acid (DNA) is not adsorbed. Due to the additional special treatment with said binding properties altering compound according to the present invention, the specificity of the nucleic acid binding matrix is altered such that less DNA is bound by the nucleic acid binding matrix thereby considerably lowering the amount of DNA contaminations in the purified RNA sample. Then, the double stranded nucleic acid flowing out can be further processed with per se known methods if desired. After optionally performing washing steps, the single stranded nucleic acid adsorbed on the nucleic acid binding matrix is eluted under conditions of low ionic strength or with water. The non-adsorbed double stranded nucleic acid collected can be further purified, for example by subsequently adjusting the fraction with an appropriate aqueous mixture of salts, especially chaotropic substances, and materials containing alcohol groups and such conditions that the double stranded nucleic acid becomes adsorbable to a second nucleic acid binding matrix and, after optionally performing washing steps, becomes elutable under conditions of low ionic strength or with water.

Other embodiments for isolating RNA are e.g. described in detail in US 2002/0081619, herein incorporated by reference. US 2002/0081619 also describes suitable examples of silica support materials, silica particles, lysis buffers, binding buffers and washing buffers which can all be used in the context of the present invention and are thus herein fully incorporated by reference. The same applies to the described detailed protocols for isolating either RNA or DNA from a sample, which are also incorporated herein by reference. Also WO 2005/045030 describes suitable lysis and washing buffers. The disclosure is also herein incorporated by reference. These known protocols are improved according to the teaching of the present invention by treating the nucleic acid binding matrix with said binding properties altering compound comprising a metal substance selected from the group consisting of metals of the main groups 13 to 16, semimetals and transition metals which leads to considerably purer isolates by reducing the amount of non-target nucleic acid contaminations.

The samples/sources containing the target nucleic acids to be isolated with the process according to the present invention may include, for example, solutions comprising the target nucleic acid, biological samples such as cells, cell cultures, tissues of all kind, body fluids of all kinds, such a blood, plasma, serum, urine, faeces; microorganisms such as bacteria, viruses, such a cytomegaly virus, HIV, hepatitis B, hepatitis C, hepatitis delta-virus; plants, plant parts, embryos, germs, fruits, funghi or mixtures containing nucleic acids following enzymatic reactions, such as in vitro transcription and/or cDNA synthesis and/or reverse transcription with subsequent polymerase chain reaction (PCR).

Also provided with the present invention is the use of a nucleic acid binding matrix for isolating a target nucleic acid from a sample comprising said target nucleic acid, wherein according to one embodiment said nucleic acid binding matrix is or has been treated with at least one compound comprising a metal substance selected from the group consisting of metals of the main groups 13 to 16, semimetals and transition metals.

According to an alternative embodiment, said nucleic acid binding matrix is at least partially derivatised with hydrophobic groups. Suitable examples and derivatizing methods for obtaining respective nucleic acid matrices are described above.

As outlined in detail above, the treatment of the nucleic acid binding matrix with said compound has the advantage, that contaminations—especially with non-target nucleic acids—are reduced. For this purpose the matrix is or has been treated as described above in detail. Further details regarding the compounds, the pre-treatment methods, solution concentrations, buffers, nature of the nucleic acid binding matrix and the like were outlined in detail above. We thus refer to the above disclosure in order to avoid repetitions.

Also within the scope of the present invention is the use of at least one compound, comprising a substance selected from the group consisting of metals of the main groups 13 to 16, semimetals and transition metals for the preparation of a nucleic acid binding matrix. As outlined in detail above said treatment has the effect that target nucleic acids such as e.g. RNA can be obtained with much higher purity, e.g. comprising less gDNA contaminations. As further details regarding the compounds, the pre-treatment methods, solution concentrations, buffers, nature of the nucleic acid binding matrices and the like were outlined in detail above, we refer to the above disclosure in order to avoid repetitions.

Also within the scope of the present invention is a nucleic acid binding matrix obtainable by contacting said nucleic acid binding matrix with a compound comprising a metal substance selected from the group consisting of metals of the main groups 13 to 16, semimetals and transition metals.

Said nucleic acid binding matrix is for example obtainable by incubating said nucleic acid binding matrix in a liquid solution containing said compound comprising a metal substance selected from the group consisting of metals of the main groups 13 to 16, semimetals and transition metals (see above).

According to a different embodiment, said nucleic acid binding matrix is reacted with said compound comprising a metal substance selected from the group consisting of metals of the main groups 13 to 16, semimetals and transition metals in the gas phase.

According to a further embodiment said modification of the binding properties of said nucleic acid matrix is achieved by adding said compounds comprising a substance selected from the group consisting of metals of the main groups 13 to 16, semimetals and transition metals to a liquid solution which is then applied to the nucleic acid binding matrix. Said solution can for example be a pre-treatment buffer comprised in a kit or for example the used lysis and/or the binding buffer (see above).

All these methods provide a nucleic acid binding matrix having altered binding properties that allow the isolation of a target nucleic acid, especially RNA, having less contaminations such as e.g. non-target nucleic acids (especially gDNA in case of RNA preparations). A combination of these nucleic acid binding matrix treatments leads to synergistic effects and is thus advantageous. Further details regarding the compounds, the pre-treatment methods, solution concentrations, buffers, nature of the nucleic acid binding matrices and the like were outlined in detail above. We thus refer to the above disclosure in order to avoid repetitions.

Any of the compositions described herein may be comprised in a kit. Also provided with the present invention is a kit for isolating a target nucleic acid from a sample comprising said target nucleic acid, comprising
  a) a nucleic acid binding matrix which
    (i) is optionally pre-treated with at least one compound comprising a metal substance selected from the group consisting of metals of the main groups 13 to 16, semimetals and transition metals, wherein said compound may also be used in dissociated or solvated form or in form of a salt, in order to reduce contaminations; and/or
    (ii) carries hydrophobic groups;
  b) optionally a solution for altering the binding properties of the nucleic acid binding matrix in order to reduce contaminations, wherein said solution comprises at least one compound comprising a metal substance selected from the group consisting of metals of the main groups 13 to 16, semimetals and transition metals;
  c) a lysis and/or binding solution containing at least one compound comprising a metal substance selected from the group consisting of metals of the main groups 13 to 16, semimetals and transition metals in order to reduce non-target nucleic acid contaminations;
  d) optionally a washing solution;
  e) optionally a solution for eluting the target nucleic acid from the nucleic acid binding matrix;
wherein at least one of the options a), b) or c) is fulfilled in order to specifically alter the nucleic acid binding properties of said nucleic acid binding matrix in order to reduce contaminations (such as non-target nucleic acids as e.g. genomic DNA) in the isolated target nucleic acid preparation. As a combination of these treatments lead to a synergistic effect regarding a reduction of contaminations, it is possible to combine said options such as e.g. option a) (i) and/or (ii) and b) or option a) and c) or option b) and c).

Further details regarding the compounds, the pre-treatment methods, solution concentrations, buffers, nature of the nucleic acid binding matrices and the like were outlined in detail above. We thus refer to the above disclosure in order to avoid repetitions.

In a non-limiting example, reagents for lysing cells, extracting RNA from the cell lysate, and/or analysing and/or quantifying the RNA obtained may be included in such a kit. The kits will thus comprise, in suitable container means, any of the reagents disclosed herein. It may also include one or more buffers or solutions, such as an appropriate lysis buffer, binding buffer, solutions to have alcohol added, elution solutions, washing solutions and other components suitable for isolating the desired RNA.

The components of the kit may be packaged either in aqueous media or in lyophilised form. The container means of the kits would generally include at least one vial, test tube, flask, bottle, syringe or other container means, into which a component may be placed, and preferably, suitably aliquoted. Were there are more than one component in the kit (they may be packaged together) the kit also will generally contain a second, third or other additional container into which the additional components may be separately placed. The kits of the present invention also may include means for containing the nucleic acid, especially RNA, and other reagent containers in close confinement for commercial sale. Such containers may include plastic containers into which the desired vials are retained. When the components of the kits are provided, in one and/or more liquid solutions, an aqueous solution, especially a sterile aqueous solution being particular preferred.

However, the components of the kit may also be provided as dry powder(s). When reagents and/or components are provided as a dry powder, the powder can be reconstituted by the addition of a suitable solvent. It is envisioned that the solvent may also be provided in another container means. The container means will generally include the ones described above. The kits may also comprise a second container means for containing a sterile, pharmaceutically acceptable buffer and/ or other diluent.

Such kits may also include components that preserve or maintain the nucleic acid, especially the sensitive RNA or that protect it against degradation. Such components may be RNase-free or protect against RNase. Such kits generally will comprise, in suitable means, distinct containers for each individual reagent or solution.

A kit will also usually include instructions for employing the kit components as well as the use of any other reagent not included in the kit. Instructions may include variations that can be implemented.

The methods, compounds and kits of the present invention may be used in various fields of research and development and may also be used for diagnostic and clinical purposes.

EXAMPLES

The following examples are included to demonstrate preferred embodiments of the present invention. It should be appreciated by those of skill in the art that the techniques disclosed in the subsequent examples represent techniques discovered by the inventors to function well on the practice of the invention, and thus can be considered to constitute preferred modes for its practice. However, those of skill in the art should, in the light of the present disclosure, appreciate that many changes can be made in the specific embodiments which are disclosed and still obtain a like or similar result without departing from the spirit and the scope of the present invention.

Example 1

Single membrane samples having a diameter of 7,5 mm where punched out of a role of silica membrane of the kind that is usually used in the commercially available RNeasy kit. Said silica membrane thus constitutes a nucleic acid binding matrix usually employed for isolating RNA. Said membrane samples were incubated for four hours at room temperature in a titanium (IV)-chloride solution (5%) in tetrahydrofuran (THF) (Merck, Darmstadt). The membrane samples were placed on a filter and were washed five times in water before they were dried for 20 hours at 40° C. in a drying chamber. The respectively treated/coated membrane samples were placed by hand as quires in an RNeasy column structure comprising a frit and a tension ring. Untreated membranes were also placed in an RNeasy column comprising a frit and a tension ring and used as a control.

Total RNA was isolated by using these columns from 10 mg rat kidney by using the RNeasy-protocol (Qiagen, Hilden). Photometric determination of the yield showed a nucleic acid yield of approximately 14 µg per 10 mg rat kidney for the columns that were pre-treated with titanium (IV)-chloride and a nucleic acid yield of approximately 9 µg per 10 mg rat kidney when using the untreated control columns. In order to analyse the quality and the purity of the extracted total RNA, 1 µl of the eluates were analysed on an Agilent 2100 Bioanalyzer (Agilent, Böblingen) using the manufacturer's protocol. The profile of the total RNA isolated with the titanium (IV) chloride pre-treated column was compared with the profile of an untreated control column (FIGS. 1 and 2).

Figure 2:
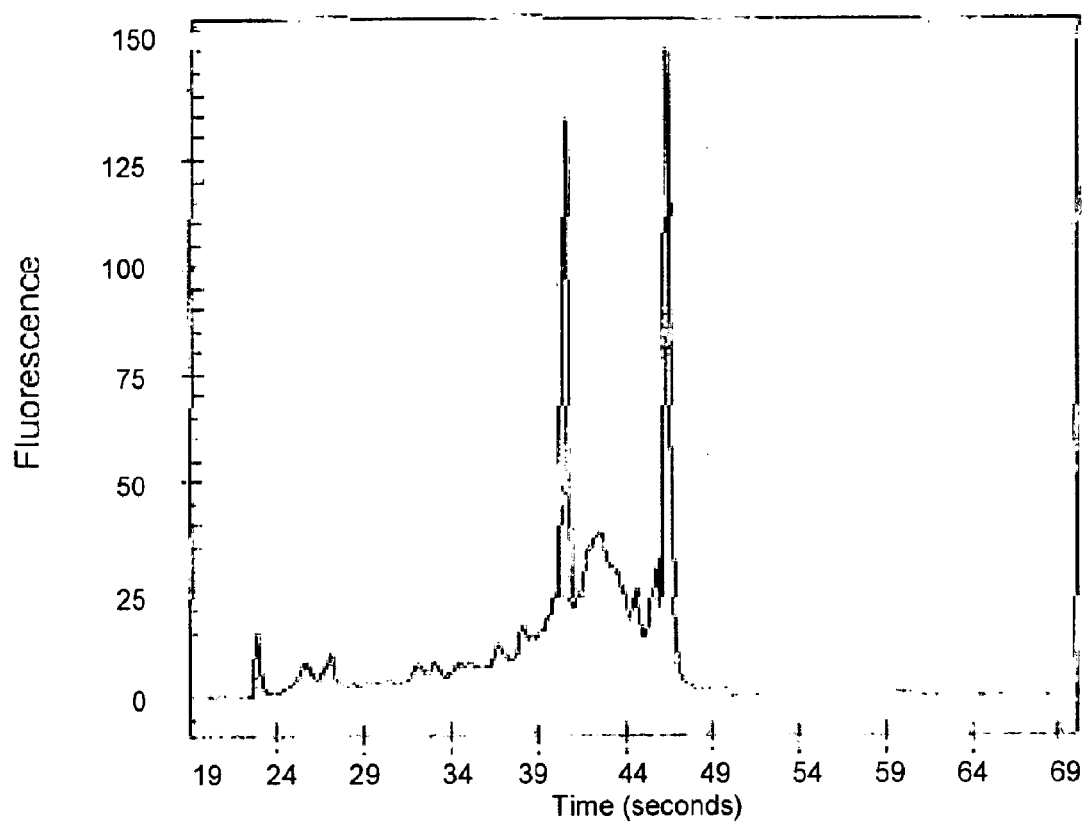
FIG. 2 shows a profile of an eluate of an untreated control column analysed on an Agilent 2100 Bioanalyzer as described in Example 1.

FIG. 1 shows that the profile of the eluate of the titanium (IV) chloride pre-treated column shows besides the peak caused by the solvent front only the two peaks which represent the 18 S and the 28 S rRNA. Genomic DNA would be detectable as an elevated profile line between the two rRNA peaks. However, the profile line of the probe isolated according to the method of the present invention returns between these two rRNA peaks to the base line. This indicates that there is no genomic DNA detectable in the isolated RNA probe which was purified according to the method of the present invention. In contrast, the untreated control column (FIG. 2) shows a clear elevation of the profile line between the 18 S and the 28 S rRNA peak. This indicates that the RNA probe which was isolated according to the protocol known in the state of the art still contains detectable traces of genomic DNA.

This proves that the incubation of the nucleic acid binding matrix, according to this example a common silica matrix, in a liquid solution comprising a transition metal compound, here titanium (IV) chloride, has the effect that genomic DNA contaminations are considerably lowered in the RNA eluates compared to the standard protocol. If there were any genomic DNA traces left there are at least not detectable on an Agilent 2001 Bioanalyzer.

Example 2

The treatment of the silica membrane was similarly performed as described in example 1. However, in contrast a zirconium chloride solution (1%) in THF was used instead of a titanium (IV) chloride solution. A comparative RNA isolation and purification was performed after assembling the membranes pre-treated according to the teaching of the present invention in an RNeasy column. Untreated columns were used as a control, which were either assembled by hand or mechanically.

$10^6$ HeLa cells were used as RNA source. Isolation was again performed according to the well established RNeasy protocol. The photometric determination of the total nucleic acid yield gave for mechanically produced untreated RNeasy columns approximately 275 µg, approximately 240 µg for the untreated reference columns, which were assembled by hand and approximately 190 µg for the columns comprising a nucleic acid binding matrix which was pre-treated with zirconium chloride.

Figure 3:
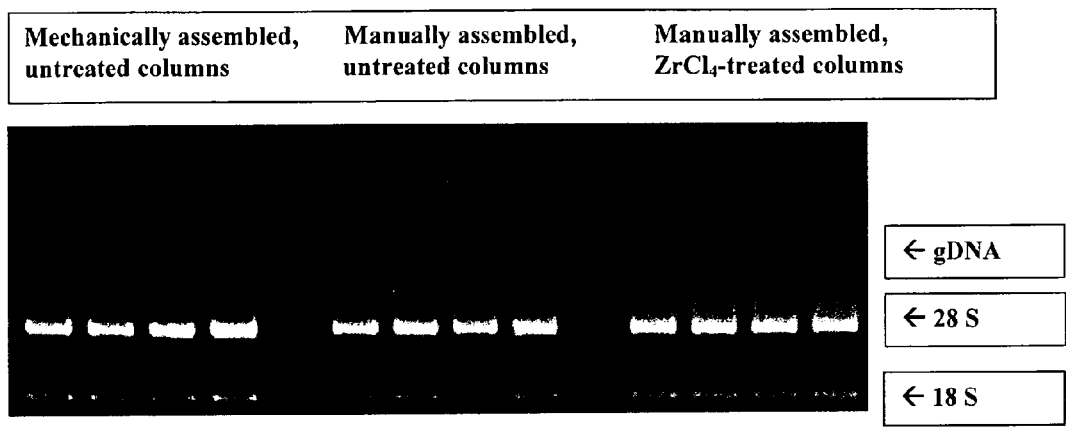
FIG. 3 shows a formaldehyde gel (1%) of eluates generated as described in Example 2.

8 µl of the eluates were applied to a formaldehyde gel (1%) in order to perform a fourfold determination in order to determine the purity and integrity of the isolated RNA (FIG. 3). FIG. 3 clearly demonstrates that non-degraded RNA was obtained with all three column types. No degradation was detectable, as the 18 S as well as the 28 S rRNA remained intact. However, the samples which were isolated by the mechanically produced untreated reference columns or by the untreated reference columns assembled by hand showed above the rRNA bands a further band which indicates a contamination of these samples with traces of genomic DNA. A respective band was not detectable with the RNA probes that were obtained from the column which was pre-treated according to the teaching of the present invention with zirconium chloride. The depletion of genomic DNA is thus more efficient when using a nucleic acid binding matrix which was pre-treated with zirconium chloride compared to the untreated reference matrices. The nucleic acid yield which was slightly less for the pre-treated columns which were assembled by hand compared to the untreated manually manufactured columns is attributable at least in part to the slight amounts of protracted genomic DNA in the eluate. Furthermore, the RNA yields sometimes also vary from isolation to isolation.

Thus also the treatment of a nucleic acid binding matrix with a zirconium chloride solution (1%) has the effect that genomic DNA contaminations are considerably lowered when using an identical RNA isolation protocol.

Example 3

The three column types described in example 2 were also used in order to isolate total RNA from $10^6$ Jurkat cells (which is a cell line derive from human T-cell leukaemia). Isolation was again performed according to the standard RNeasy-protocol (Qiagen, Hilden). 5 ng of the total nucleic acid obtained after isolation was used in a quantitative RT-PCR (reverse transcription PCR) for determining the overall nucleic acid concentration (thus RNA and DNA). Furthermore, a quantitative PCR was performed in order to be able to determine the concentration of genomic DNA in the probe. During a quantitative PCR no RNA is amplified/detected as the reverse transcription step (leading to cDNA which can be amplified by PCR) is missing. Taqman beta-Actin Control Reagents (Applied Biosystem, Foster City) were used as primers and probes. Afterwards, the Ct-value was determined for each reaction. The Ct-value (threshold cycle) describes the amplification cycle of the reaction, wherein the fluorescence is elevated significantly over the background fluorescence (also known as crossing point). The Ct-value may be used as a measure for contamination with genomic DNA in a probe. When a quantitative PCR is performed using an RNA preparation as template only the genomic DNA contaminations are amplified as the DNA polymerases used in PCR are DNA dependent and thus do not amplify RNA. The more cycles are needed in order to reach the Ct-value, the less genomic DNA contaminations are present in the RNA preparation. Conversely, the less cycles are needed in order to reach the Ct-value, the more genomic DNA contaminations are present in the sample. The determination of the Ct-values when performing a quantitative PCR led to the following results for the column types used:

| Tested columns | Ct-value |
|---|---|
| mechanically assembled, untreated | 25.05 |
| manually assembled, untreated | 25.02 |
| manually assembled, pre-treatment with zirconium chloride | 28.48 |

Already by analysing the Ct-values it becomes readily apparent that the sample purified with a column treated according to the teachings of the present invention contained less genomic DNA as more cycles were needed before the Ct-value was reached.

Even more significant information on the genomic DNA contamination may be obtained when determining the Δ (delta) Ct-value of a probe. The determination of the delta Ct-value is a standardisation of the RNA concentration compared to the total nucleic acid concentration in the eluates. This as the Ct-values obtained from the quantitative PCR are subtracted from the Ct-values obtained from the quantitative RT-PCR (quantifying RNA and DNA). The higher the delta Ct-value the less DNA contaminations are present in the probe. The results were as follows:

| Tested Columns | Delta Ct-value |
|---|---|
| mechanically assembled, untreated | 6.03 |
| manually assembled, untreated | 5.51 |
| manually assembled, pre-treatment with zirconium chloride | 9.87 |

The considerably higher delta Ct-value obtained when using a column which was pre-treated according to the teachings of the present invention demonstrates that said probe contained much less genomic DNA contaminations than the samples obtained with standard columns.

Thus also the use of the very sensitive quantitative RT-PCR and the quantitative PCR demonstrates the efficient depletion of genomic DNA when treating the nucleic acid binding matrix with a compound comprising a metal substance selected from the group consisting of metals of the main groups 13 to 16, semimetals and transition metals, in the present example the transition metal zirconium in the form of chloride. Compared to the reference columns an improvement was achieved of the delta Ct-value from over 4. This corresponds to a more than 16-fold reduced genomic DNA concentration in the probe. Thus by treating the nucleic acid binding matrix with zirconium chloride, the genomic DNA was lowered in the eluates by more than 16-fold when applying an otherwise identical standard RNA isolation protocol.

Example 4

The treatment of the silica containing nucleic acid binding matrix was performed as described in example 1, with the difference that this time the compounds $FeCl_2$, $FeCl_3$ and $SnCl_2$ were used in concentrations ranging from 0.1% to 2.5% in THF for altering the binding properties of the nucleic acid binding matrix. An RNA isolation procedure was used as described in example 3 with the difference, that this time $10^6$ HeLa cells were used as biological source for RNA. For determination of genomic DNA contaminations a quantitative PCR as well as a quantitative RT-PCR was performed using Taqman beta-Actin Control Reagents (Applied Biosystems, Foster City). The following Ct-values were determined in the quantitative PCR, when 5 ng of the overall nucleic acid was used from the eluates:

| Columns | Ct-value |
| --- | --- |
| Untreated | 26.72 |
| treated with 0.1% $FeCl_2$ | 28.55 |
| treated with 0.5% $FeCl_2$ | 28.40 |
| treated with 1% $FeCl_2$ | 29.28 |
| treated with 2.5% $FeCl_2$ | 28.93 |
| treated with 0.1% $FeCl_3$ | 27.29 |
| treated with 0.5% $FeCl_3$ | 29.63 |
| treated with 1% $FeCl_3$ | 29.06 |
| treated with 2.5% $FeCl_3$ | 28.14 |
| treated with 0.1% $SnCl_2$ | 29.62 |
| treated with 0.5% $SnCl_2$ | 31.55 |
| treated with 1% $SnCl_2$ | 29.45 |
| treated with 2.5% $SnCl_2$ | 30.04 |

The determined Ct-values demonstrate that the treatment of the nucleic acid binding matrix with the different tested compound solutions led in all cases to a considerable depletion of genomic DNA contaminations when using lower compound concentrations.

This conclusion can be drawn as explained above from the elevated Ct-values compared to the untreated control nucleic acid binding matrix, indicating less genomic DNA contaminations. The difference observed in this experiment was up to 5 Ct-values, which corresponds to a depletion of genomic DNA of approximately 32-fold.

Example 5

RNA was isolated from 1 mg and 5 mg rat kidney according to the RNeasy-protocol using the stannous(II) chloride treated silica nucleic acid binding matrices described in example 4. An identical untreated reference nucleic acid binding matrix was used as a control. A quantitative PCR was performed using the rat c-jun kit of Applied Biosystems (Foster City). The following Ct-values were determined, when 5 ng total nucleic acid was used from the eluates:

| Columns | Ct-value 1 mg tissue | Ct-value 5 mg tissue |
| --- | --- | --- |
| Untreated | 28.16 | 29.07 |
| treated with 0.1% $SnCl_2$ | 30.25 | 30.73 |
| treated with 0.5% $SnCl_2$ | 33.12 | 34.33 |
| treated with 1% $SnCl_2$ | 33.22 | 35.11 |
| treated with 2.5% $SnCl_2$ | 33.06 | 32.67 |

The treatment of the nucleic acid binding matrices with stannous (II) chloride led in all cases to a clear reduction of genomic DNA contaminations. In this experiment differences up to 6 Ct-values were observed, which corresponds to a depletion of genomic DNA of approximately 64-fold.

Example 6

Total RNA was isolated from 1 mg rat kidney using untreated, mechanically produced RNeasy-columns. Some of the columns were activated before the nucleic acid containing lysate was applied onto the column by using 0.1%, 0.5% or 1% stannous(II)-chloride solution in THF. 500 μl of the respective stannous(II) chloride solution were applied to the untreated nucleic acid binding matrix of the columns. The columns were centrifuged for 1 min. at 10.600×g and dried for 5 min at room temperature. Afterwards the standard RNeasy-protocol was performed. A quantitative PCR and a quantitative RT-PCR was performed with the primers and the probes according to example 5 and the delta Ct-value was determined:

| Protocol/Column | Delta Ct-value |
| --- | --- |
| RNeasy - untreated | 4.73 |
| RNeasy activated with 0.1% $SnCl_2$ | 5.53 |
| RNeasy activated with 0.5% $SnCl_2$ | 6.23 |
| RNeasy activated with 1% $SnCl_2$ | 7.37 |

These experiments also demonstrate that the pre-treatment of the nucleic acid binding matrix with a compound comprising a metal substance selected from the group of metals of the main groups 13 to 16, semimetals and transition metals as for example stannous(II) chloride leads to a favourable activation of the nucleic acid binding matrix leading to a considerable reduction of contaminations with genomic DNA when following the usual RNA isolation protocol. The obtained results are comparable to the longer silica matrix pre-treatment methods described in example 1. This demonstrates the suitability of the present invention to quickly modify nucleic acid binding matrices in order to isolate purer target nucleic acids from a sample.

Example 7

Total RNA was isolated from 5 mg rat kidney by using normal untreated, mechanically produced RNeasy-columns. The RNeasy-protocol was used for RNA isolation. However, for some of the preparations 0.1 mM, 1 mM, 5 mM and 10 mM stannous(II) chloride was added to the buffer RLT of the RNeasy kit, which is the regular lysis and binding buffer of the RNeasy-protocol. The determination of the delta Ct-values was performed as indicated in example 6:

| Protocol/Column | Delta Ct-value |
| --- | --- |
| 0 mM $SnCl_2$ in buffer RLT | 3.77 |
| 0.1 mM $SnCl_2$ in buffer RLT | 4.81 |
| 1 mM $SnCl_2$ in buffer RLT | 5.75 |
| 5 mM $SnCl_2$ in buffer RLT | 6.74 |
| 10 mM $SnCl_2$ in buffer RLT | 5.74 |

Example 7 clearly demonstrates that adding a compound comprising a metal substance selected from the group consisting of metals of the main groups 13 to 16, semimetals and transition metals such as stannous(II) chloride to the lysis and/or binding buffer also leads to a considerable lowered contamination of genomic DNA when isolating RNA from a nucleic acid containing source. The results are again comparable to the longer pre-treatment as described in example 1.

Example 8

Stannous(II)-chloride pre-treated nucleic acid binding matrices were used for isolating total RNA. The production of the modified nucleic acid binding matrices was performed as described in example 4. Silica matrices were used, which were coated/pre-treated with a stannous(II)-chloride solution (1%). In order to analyse synergistic effects, the pre-treated silica matrices were additionally treated with a stannous(II)-chloride solution directly prior to performing the RNA isolation protocol. Thus 0.1 mM, 1 mM, 5 mM and 10 mM stannous(II)-chloride was added additionally to the lysis and binding buffer. The RNA was isolated from $10^7$ Jurkat cells per preparation. The determination of the delta Ct-value was performed as described in example 3:

| Protocol/Column | Delta Ct-value |
| --- | --- |
| untreated, buffer RLT | 6.28 |
| treated with 1% SnCl$_2$, buffer RLT | 8.23 |
| treated with 1% SnCl$_2$, buffer RLT + 0.1 mM SnCl$_2$ | 10.20 |
| treated with 1% SnCl$_2$, buffer RLT + 1 mM SnCl$_2$ | 9.60 |
| treated with 1% SnCl$_2$, buffer RLT + 5 mM SnCl$_2$ | 9.77 |
| treated with 1% SnCl$_2$, buffer RLT + 10 mM SnCl$_2$ | 11.47 |

This experiment clearly demonstrates that the combined use of a pre-treated nucleic acid binding matrix with a lysis and/or binding buffer containing a compound comprising a metal substance selected from the group consisting of metals of the main groups 13 to 16, semimetals and transition metals such as for example stannous(II)-chloride leads to an even further improved depletion of genomic DNA when isolating RNA from complex biological sources comprising different types of nucleic acids.

Example 9

Two different kinds of commercially available magnetic silica beads were used as a nucleic acid binding matrix (MagAttract B and MagAttract G—Qiagen) as an alternative to a silica membrane. The beads were incubated separately from each other over night in a solution comprising SnCl$_2$ (1%) in THF. $10^6$ Jurkat cells per preparation were lysed and homogenised using the buffer RLT (Qiagen) the next day. Afterwards, ethanol as well as 50 µl of the magnetic suspension was added to the lysed cells. The binding preparation was incubated for 5 min at room temperature. The supernatant was discarded after magnetic separation and the magnetic particles were afterwards washed once in the buffer AW1 and twice in the buffer RPE. Elution was performed with 200 µl RNase free water. The delta Ct-values were determined as described in example 3:

| Magnetic beads | Delta Ct-value |
| --- | --- |
| MagAttract B, untreated | 3.89 |
| MagAttract B, incubated in SnCl$_2$ | 7.11 |
| MagAttract G, untreated | 3.58 |
| MagAttract G, incubated in SnCl$_2$ | 5.69 |

This experiment also clearly demonstrates the efficiency of the method according of the present invention which may also be used on spheric molecules such as for example magnetic beads. Also the other protocols described above for treating the nucleic acid binding matrices may be used for this application.

Example 10

A reference example was also performed in order to demonstrate that the effects obtained with the teachings of the present inventions are considerably improved compared to teachings known in the state of the art. E.g. EP 0 818 461 discloses that adding lithium salts to chaotropic salts is supposed to modify the selectivity of the nucleic acid binding carrier for RNA adsorption thereby leading to lowered DNA contaminations. However, as demonstrated below, alkaline metals such as lithium chloride are not suitable in order to alter the binding properties of a standard nucleic acid binding matrix such that an improvement, as seen with the compounds used according to the present invention, is obtained. As is demonstrated below, lithium chloride did not alter the amount of gDNA contaminations in the purified RNA sample.

Total RNA was extracted according to the standard RNeasy protocol from $10^6$ Jurkat cells using mechanically produced RNeasy columns per test sample. 0.1 mM, 1 mM, 5 mM, 10 mM, 50 mM, 100 mM, 250 mM, 500 mM and 1 M LiCl were added to the lysis and binding buffer RLT. No lithium chloride (0 mM LiCl) was added to the control. The quantification of genomic DNA contamination was performed as described in example 3. The results were as follows:

| Columns | Ct-value |
| --- | --- |
| 0 mM LiCl | 26.78 |
| 0.1 mM LiCl | 27.05 |
| 1 mM LiCl | 27.30 |
| 5 mM LiCl | 27.06 |
| 10 mM LiCl | 27.26 |
| 50 mM LiCl | 27.49 |
| 100 mM LiCl | 26.93 |
| 250 mM LiCl | 26.92 |
| 500 mM LiCl | 26.94 |
| 1 M LiCl | 26.17 |

As can be seen from the Ct-values, the addition of lithium chloride did not result in a reduction of genomic DNA in the isolated RNA preparation. The addition of lithium chloride thus did not have any effect on the degree of contamination with non-target nucleic acid. The quantitative PCR resulted with all tested lithium chloride concentrations in approximately the same Ct-values which only varied statistically. This demonstrates that the addition of the alkaline metal lithium chloride does not have any beneficial effect on depletion of genomic DNA in RNA preparations as is seen with the teachings according to the present invention.

Example 11

A further reference example was performed in order to demonstrate the special effects that are associated with the teachings of the present invention.

The experiment was performed as described in Example 10. However, instead of LiCl, MgCl$_2$ and CaCl$_2$ was added to the buffer RLT in order to generate reference samples. The following concentrations were used: 0 mM, 0.1 mM, 1 mM, 5 mM, 10 mM, 50 mM, 100 mM, 250 mM, 500 mM and 1 M. The quantification of contamination of the RNA eluates with genomic DNA was performed as described in Example 3.

| Concentration | CT-value for MgCl$_2$ | CT-value for CaCl$_2$ |
| --- | --- | --- |
| 0 mM | 30.20 | 30.01 |
| 0.1 mM | 30.84 | 30.29 |
| 1 mM | 30.76 | 30.44 |
| 5 mM | 30.78 | 30.37 |
| 10 mM | 30.54 | 30.47 |
| 50 mM | 30.30 | 30.19 |
| 100 mM | 30.21 | 29.01 |
| 250 mM | 28.99 | 27.88 |

| Concentration | CT-value for MgCl$_2$ | CT-value for CaCl$_2$ |
|---|---|---|
| 500 mM | 28.27 | 27.10 |
| 1 M | 28.20 | 27.00 |

The results demonstrate that the addition of small amounts of MgCl$_2$ and CaCl$_2$ to the binding buffer RLT does not have a positive effect on the reduction of DNA contaminations. These alkaline earth metals do not reduce non-target contaminations as is the case with the compounds that are used according to the teachings of the present invention such as e.g. stanneous chloride (see above). Furthermore, when using higher concentrations of MgCl$_2$ and CaCl$_2$ in the binding buffer RLT, a negative effect on contaminations is observed as the amount of genomic DNA contaminations even increased. The contamination with genomic DNA was up to a factor 8 higher (equals 3 CT-values).

Example 12

Three different kinds of commercially available magnetic silica beads were used as nucleic acid binding matrix (MagAttract B, MagAttract G and MagAttract E solution—QIAGEN). Two mml of said beads were separated via a magnet from the storage solution. The wet magnetic particles were incubated for four hours in varying concentrations of SnCl$_2$-solutions. SnCl$_2$-solutions of 0.1%, 0.5%, 1% and 2% were used. After said incubation the beads were separated from the solutions via a magnet and the magnetic particles were dried in a dryer at 50° C. After drying said particles they were either received in water or in the RNeasy binding buffer RLT.

Using the respectively treated MagAttract B, MagAttractG and MagAttractE particles as well as untreated control particles, an RNA isolation was performed 1×10$^6$ Jurkat-cells. The cells were provided in RNeasy binding buffer RLT, were centrifuged for lysis through a QIAShredder column and were mixed with 1 Vol. 70% ethanol. After adding the respective magnetic particles, the particle/sample solution was mixed for five minutes on a plate shaker, in order to support nucleic acid binding. After magnetically separating the particles, the supernatant was collected and discarded; the magnetic particles were mixed with 750 µl washing buffer RW1 and were again shacked for five minutes. After magnetic separation, the supernatant was discarded and the particles were washed twice with 500 µl buffer RPE. Elution was performed with 100 µl water and repeated shaking for 5 min. The yield was determined spectrophotometrically, which was comparable for all treated particles that were tested (data not shown). 5 ng of the obtained eluates were used in a quantitative PCR (see example 3). The results are summarized in the subsequent table:

| Particle | Ct-value |
|---|---|
| MagAttract B (untreated control) | 22.34 |
| MagAttract B, 0.1%, contained in water | 24.66 |
| MagAttract B, 0.5%, contained in water | 25.95 |
| MagAttract B, 1%, contained in water | 25.63 |
| MagAttract B, 2%, contained in water | 27.05 |
| MagAttract B, 0.1%, contained in RLT | 24.84 |
| MagAttract B, 0.5%, contained in RLT | 27.08 |
| MagAttract B, 1%, contained in RLT | 26.94 |
| MagAttract B, 2%, contained in RLT | 26.22 |
| Mag Attract G (untreated control) | 22.24 |
| MagAttract G, 0.1%, contained in water | 22.71 |
| MagAttract G, 0.5%, contained in water | 23.28 |
| MagAttract G, 1%, contained in water | 23.41 |
| MagAttract G, 2%, contained in water | 25.05 |
| MagAttract G, 0.1%, contained in RLT | 24.19 |
| MagAttract G, 0.5%, contained in RLT | 25.67 |
| MagAttract G, 1%, contained in RLT | 24.56 |
| MagAttract G, 2%, contained in RLT | 23.93 |
| MagAttract E (untreated control) | 23.35 |
| MagAttract E, 0.1%, contained in water | 24.16 |
| MagAttract E, 0.5%, contained in water | 24.87 |
| MagAttract E, 1%, contained in water | 25.90 |
| MagAttract E, 2%, contained in water | 25.82 |
| MagAttract E, 0.1%, contained in RLT | 23.69 |
| MagAttract E, 0.5%, contained in RLT | 24.81 |
| MagAttract E, 1%, contained in RLT | 25.37 |
| MagAttract E, 2%, contained in RLT | 25.76 |

As can be seen from the obtained results, all tested pretreated magnetic particles achieved higher Ct-values as the respectively untreated control particles. Hence, the described treatments of the particles with a metal compound according to the teachings of the present invention results in a depletion of genomic DNA and therefore in an increase of purity of the isolated RNA. Already with the examples performed, up to 5 Ct-value differences could be achieved, which equals a depletion of genomic DNA contamination by 32-folds compared to untreated MagAttract particles. The results also demonstrate that the concentration of the treatment/coating influences the depletion of genomic DNA. Whether the particles were contained in water or RLT did not have an influence on the depletion of the genomic DNA.

Example 13

Single membrane samples having a diameter of 7.5 mm were punched out of a role of silica membrane of the kind that is usually used in the commercially available RNA easy kit. Said silica membrane does constitute a nucleic acid binding matrix, which is usually used for isolating/purifying RNA.

The respective membranes were especially coated/treated in order to at least partially derivatize them with hydrophobic groups. In order to achieve a respective derivatization, the membranes were treated/coated with propyltriethoxysilane (PTS) for different time periods. 57 g (91.2 g) concentrated ammonia and 10 g (16 g) distilled water were provided in a reaction bulb, filled up with absolute ethanol to 500 ml (800 ml) and were stirred slowly with a KPG-stirrer. Afterwards, the punched out membranes were added to the reaction solution and 200 µl PTS was added after 5 minutes. The membranes were incubated for different time periods in said reaction solution. Afterwards, the membranes were washed three times with VE water and were dried at 50° C. in a dryer for 4-8 h. The respectively treated membranes were afterwards assembled to a spin column. Using these columns total RNA was isolated from 1×10$^6$ Jurkat cells using the RNeasy protocol (QIAGEN, Hilden). As a control the same preparations were performed using mechanically assembled RNeasy columns and additionally, untreated RNeasy columns assembled by hand. 5 ng of the total nucleic acid obtained after purification was used in quantitative PCR in order to determine the DNA contamination using the Taqman beta-Actin Control Reagents (Applied Biosystems, Foster City). By using a respective preparation it is possible to determine, how much genomic DNA is still present as contamination in the eluted overall nucleic acid fraction. The higher the Ct-value, the less genomic DNA is present as contamination in the eluate.

The results can be summarized as follows:

| Sample | Ct-value |
|---|---|
| Mechanically assembled column, untreated | 25.72 |
| Manually assembled column, untreated | 26.03 |
| Manually assembled column, treated with PTS for 1 h | 26.98 |
| Manually assembled column, treated with PTS for 3 h | 26.51 |
| Manually assembled column, treated with PTS for 4 h | 26.86 |
| Manually assembled column, treated with PTS for 17 h | 29.18 |

The results show, that a very short incubation of the membrane with PTS only leads to a slight improvement of genomic DNA depletion. The longer the membrane is contacted with the compound providing hydrophobic groups, the better the obtained Ct-value. As can be seen from the results, the Ct-values obtained after incubation for 17 hours is considerably higher. The increase of the Ct-value by using a constant amount of nucleic acid shows, that the respectively treated matrix shows a depletion of genomic DNA by 8-fold.

Example 14

The treatment of the silica membranes was similarly performed as described in example 13. However, this time the silica matrixes were coated with octadecyltrimethoxysilane (OTM) for different time periods. In order to obtain silica matrixes which are at least partially derivatized with hydrophobic groups, 800 ml of the reaction solution described in example 13 was used for incubating the silica matrixes for 5 minutes. After adding 8, 80 or 800 µl OTM, the silica membranes were further incubated for further 4 or 24 h (c(OTM): 0.024 mmol/l to 2.4 mmol/l). Total RNA was isolated again from $10^6$ Jurkat cells. Purification, including the controls as well as the determination of the contamination with genomic DNA was performed as described in example 13. However, additionally, a further control was performed. Therein, the silica matrix was incubated for 24 h in the solvent solution without OTM, in order to exclude an effect of the solvent on the genomic DNA depletion.

The results can be summarized as follows:

| Column | Ct-value |
|---|---|
| Mechanically assembled column, untreated | 26.81 |
| Manually assembled column, untreated | 24.90 |
| Manually assembled column, incubated without OTM | 25.35 |
| Manually assembled column, treated with OTM, 4 h, 8 µl | 26.98 |
| Manually assembled column, treated with OTM, 4 h, 80 µl | 30.77 |
| Manually assembled column, treated with OTM, 4 h, 800 µl | 31.82 |
| Manually assembled column, treated with OTM, 24 h, 8 µl | 27.86 |
| Manually assembled column, treated with OTM, 24 h, 80 µl | 31.43 |
| Manually assembled column, treated with OTM, 24 h, 800 µl | 32.17 |

This experiment demonstrates, that the incubation period also influences the efficiency of genomic DNA depletion when treating the silica membranes with OTM. However, the influence is less prominent. A higher influence, however, was observed regarding the concentration of OTM used for derivatizing the silica matrix. Therein, a better efficiency was observed when the used concentration of OTM was higher. Wherein an increase from 8 µl (0.24 mmol/l) to 80 µl (2.4 mmol/l) resulted in a great difference of approximately 4 CT-values, a further increase of the concentration only resulted in an improvement of 1 CT-value. However, the yield of total nucleic acid is considerably lower, when treating the silica matrix with 800 µl OTM, wherein the total yield is in a range comparable to the control when treating the silica matrix with 80 µl OTM (data not shown). An optimized coating/derivatization can therefore obtained by adjusting the incubation period as well as the concentration, in order to obtain a highly efficient depletion of genomic DNA, by conserving an efficient/high yield of total RNA.

Example 15

The treatment was performed as described in example 13. However, this time the silica matrix was treated with hexadecyltrimethoxysilane (HMS) using different concentrations. As described in example 14, 8 µl, 80 µl and 800 µl HMS was used in 800 ml of the reaction medium described in example 13, for 24 hours. (c(HMS): 0.0256 mmol/l to 2.56 mmol/l). Total RNA was isolated in this example from $10^6$ Jurkat cells according to the RNeasy protocol. Purification including the controls was performed as described in example 14. The results can be summarized as follows:

| Column | Ct-value |
|---|---|
| Mechanically assembled column, untreated | 26.59 |
| Manually assembled column, untreated | 25.99 |
| Manually assembled column, incubated without HMS | 25.86 |
| Manually assembled column, treated with HMS, 8 µl | 29.89 |
| Manually assembled column, treated with HMS, 80 µl | 32.10 |
| Manually assembled column, treated with HMS, 800 µl | 32.49 |

This experiment demonstrates that also compounds such as HMS lead to considerable improvements regarding the specific depletion of genomic DNA relative to total RNA. A Ct-difference of up to 6 is obtainable, which equals a relative depletion of genomic DNA by 64-fold. This example also demonstrates, that the concentration of the compound, which provides the silica membrane with hydrophobic groups, influences the efficiency of depletion of genomic DNA.

Example 16

The treatment of the silica membranes was performed as described in example 15. However, this time the silica matrix was treated with the compound Octyltrimethoxysilane (OTS) using different concentrations. As described in example 14, 8 µl, 80 µl and 800 µl OTS was used in 800 ml of the reaction media described in example 13, for 24 hours with the membrane (c(OTS): 0.0321 mmol/l to 3.21 mmol/l). As described in example 13, total RNA was isolated from $10^6$ Jurkat cells and 5 ng of the obtained nucleic acid was quantified using quantitative PCR. The results can be summarized as follows:

| Column | Ct-value |
|---|---|
| Mechanically assembled column, untreated | 26.59 |
| Manually assembled column, untreated | 25.99 |
| Manually assembled column, incubated without OTS | 25.86 |
| Manually assembled column, treated with OTS, 8 µl | 25.79 |
| Manually assembled column, treated with OTS, 80 µl | 31.23 |
| Manually assembled column, treated with OTS, 800 µl | 30.90 |

In contrast to the preceding examples, the treatment with 8 µl OTS does not result in a considerable effect regarding the depletion of genomic DNA. However, an increase of the concentration to 80 or 800 µl OTS showed similar results as obtained with the compounds described before. The Ct-values achieved are between 4 and 5 higher compared to the untreated controls, which equals a depletion of genomic DNA by 16 to 30 fold.

Example 17

The treatment of the silica membrane was performed as described in example 13 using the compounds described in the examples 13 to 16. Total RNA was at this time not isolated from cell cultures, but from 1 mg or 5 mg rat liver per experiment. The RNeasy-protocol was used for isolation. Afterwards, a quantitative PCR was performed using the rat c-jun Kit from Applied Biosystems (Foster City). The following Ct-values were obtained, when 5 ng of the total nucleic acid obtained from the eluates were used:

| Column | Ct value using 1 mg rat liver | Ct value using 5 mg rat liver |
| --- | --- | --- |
| Mechanically assembled column, untreated | 31.59 | 32.95 |
| Manually assembled column, untreated | 31.77 | 31.92 |
| Manually assembled column, incubated without silane | 31.59 | 32.99 |
| Manually assembled column, treated with OTS, 80 µl, 24 h | 35.10 | 35.92 |
| Manually assembled column, treated with OTM, 44 µl, 24 h | 33.69 | 32.64 |
| Manually assembled column, treated with OTM, 80 µl, 24 h | 34.97 | 34.04 |
| Manually assembled column, treated with OTM, 44 µl, 4 h | 32.67 | 34.27 |
| Manually assembled column, treated with OTM, 80 µl, 4 h | 34.86 | 34.99 |

As can be seen from the provided examples, using a silica matrix which is at least partially derivatised with hydrophobic groups, such as the described silane compounds has a positive influence regarding depletion of genomic DNA. Again, an influence of the incubation time as well as concentration of the used compounds can be observed on the efficiency of depletion.

Example 18

The silica membranes treated with 80 µl OTM as described in example 14 were used to isolate total RNA from cell culture cells. Preparation was performed as described in example 13. However, this time $SnCl_2$ was added to the binding buffer RLT in different concentrations. By combining $SnCl_2$ with the binding buffer RLT it was evaluated whether a synergistic effect is observed in conjunction with using a nucleic acid matrix derivatised with hydrophobic groups, i.e. that genomic DNA depletion is improved. The following results were obtained:

| Column | Ct-value |
| --- | --- |
| Mechanically assembled column, untreated | 26.24 |
| Manually assembled column, untreated, 1 mM $SnCl_2$ | 27.72 |
| Manually assembled column, untreated, 5 mM $SnCl_2$ | 28.13 |

| Column | Ct-value |
| --- | --- |
| OTM | 31.02 |
| OTM + 1 mM $SnCl_2$ | 31.71 |
| OTM + 5 mM $SnCl_2$ | 32.26 |

This experiment demonstrates that both treatments (OTM and $SnCl_2$) lead to a considerable depletion of genomic DNA contaminations. However, also a synergistic effect is observed. This synergistic effect observed with 5 mM $SnCl_2$ results in a 2-fold depletion of genomic DNA.

The invention claimed is:

1. A method for isolating a target nucleic acid from a sample, said method comprising:
   (a) providing a nucleic acid binding matrix comprising a silica surface, wherein:
      (i) the nucleic acid binding matrix is treated or has been treated with at least one compound comprising a metal substance selected from the group consisting of metals of the main groups 13 to 16, semimetals, and transition metals, wherein said compound is optionally in dissociated form, solvated form or in a form of a salt; and
      (ii) the nucleic acid binding matrix has been derivatized with a silane compound carrying at least one hydrophobic group;
   (b) contacting the nucleic acid binding matrix with the sample; and
   (c) obtaining said target nucleic acid from said nucleic acid binding matrix, wherein at least part of the target nucleic acid binds directly to the silica surface.

2. A method according to claim 1, wherein a binding solution is used which comprises a chaotropic agent.

3. A method according to claim 1, wherein said target nucleic acid is bound by adsorption.

4. A method according to claim 1, wherein said compound comprises a metal substance selected from the group consisting of Sn, Fe, Zr, Ta, Ti, Al and Ge.

5. A method according to claim 1, wherein said compound comprising a metal substance is used in a form of a salt, a salt complex and/or in a form of a hydrolysable compound.

6. A method according to claim 5, wherein said compound is used in a form of a salt, and further wherein anions are used which are selected from the group consisting of halogenides, pseudohalogenides, nitrates, phosphates, sulphates and the conjugated bases of organic acids.

7. A method according to claim 5, wherein said compound is selected from the group consisting of zirconium chloride, titanium (IV) chloride, aluminium chloride, stannous chloride, ferrous (II) chloride, ferric (III) chloride, aluminium isopropoxide, titanium isopropoxide, zirconium isopropoxide, chlorotriisopropyl orthotitanate, triisopropylborate, zirconium isopropoxide isopropanol-complex, zirconium oxide chloride, aluminium triisopropylate and tantalum pentachloride.

8. A method according to claim 1, wherein said nucleic acid binding matrix is contacted with said compound comprising a metal substance according to at least one of the following methods:
   (a) immersing said nucleic acid binding matrix in a solution comprising said at least one compound comprising a metal substance and drying said immersed nucleic acid binding matrix; and/or (b) reacting said nucleic acid binding matrix with said at least one compound comprising a metal substance in the gas phase; and/or
(c) adding said at least one compound comprising a metal to a liquid solution which is applied to the nucleic acid binding matrix prior to performing the nucleic acid isolation from the sample, and wherein said sample comprises at least two different kinds of nucleic acids; and/or
(d) adding said at least one compound comprising a metal to a lysis and/or binding buffer used for nucleic acid isolation.

9. A method according to claim 8, wherein said nucleic acid binding matrix treatments are further specified as follows:
(a) said immersion solution comprises said compound comprising a metal in a concentration of at least 0.05%, and wherein said substance is selected from the group consisting of zirconium, titanium, tantalum, aluminium, boron, germanium, iron and tin and/or
(c) a pre-treatment solution comprises said compound comprising a metal substance in a concentration of at least 0.05%, and wherein said compound is a stannous or a ferric or ferrous compound and/or
(d) a lysis and/or binding buffer comprises said compound in a concentration of at least 0.05 mM and wherein said compound is a stannous or a ferric or ferrous compound.

10. Method according to claim 1, wherein the hydrophobic group comprises a substituted or unsubstituted alkyl substituent having a length of from 1 to 50 C-atoms, wherein said alkyl substituent may have a branched or linear structure.

11. Method according to claim 1, wherein said silane compound is selected from the group consisting of:
reactive silane compounds comprising at least one hydrophobic group monofunctional, bifunctional or trifunctional silane compounds comprising at least one hydrophobic group
alkoxysilane compounds, halosilane compounds or aminosilane compounds comprising at least one hydrophobic group, and

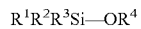

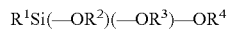

or

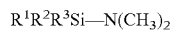

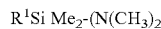

wherein $R^1$, $R^2$, $R^3$, and/or $R^4$ have the same or a different meaning and are independently selected from the group consisting of hydrogen, alkyl substituent, alkylene substituent and a functional group, and wherein at least one of $R^1$, $R^2$, $R^3$, and/or $R^4$ is an alkyl substituent having a length of 1 to 50 C-atoms which may be substituted or unsubstituted.

12. Method according to claim 11, wherein said at least one compound used for modifying said nucleic acid binding matrix with hydrophobic groups is selected from the group consisting of propyltriethoxysilane (PTS), octadecyltrimethoxysilane (OTM), hexadecyltrimethoxysilane (HMS), octyltrimethoxysilane (OTS), tetradecyltrimethoxysilane and octadecyltrimethoxysilane.

13. A method according to claim 1, wherein
said sample comprising said target nucleic acid is lysed,
a complex of the target nucleic acid and said nucleic acid binding matrix is formed,
if a lysis buffer is used, optionally a lysis buffer mixture is removed from a resulting complex,
a resulting complex is optionally washed, and/or
the target nucleic acid is obtained from the complex.

14. The method according to claim 1, wherein said nucleic acid binding matrix is magnetic and wherein said matrix carries a bound target nucleic acid and is isolated from the liquid phase using a magnetic field.

15. Method according to claim 1, wherein a nucleic acid binding matrix is used which carries hydrophobic groups.

16. The method of claim 1 wherein the nucleic acid binding matrix is treated with the at least one compound comprising the metal substance prior to or simultaneously with step (b).

17. The method of claim 1, wherein:
(a)(iii) said nucleic acid binding matrix is capable of binding the target nucleic acid in the absence of the treatments according to (a)(i)-(a)(ii); and
(a)(iv) treatment of the nucleic acid binding matrix with the at least one compound comprising the metal substance increases the ability of the nucleic acid matrix to purify the target nucleic acid relative to at least one non-target nucleic acid.

18. The method of claim 17, wherein the target nucleic acid comprises RNA and the non-target nucleic acid comprises DNA.

19. A method for isolating a target nucleic acid from a sample, said method comprising:
(a) providing a nucleic acid binding matrix comprising a silica surface and at least one hydrophobic group;
(b) contacting the nucleic acid binding matrix with the sample; and
(c) obtaining said target nucleic acid from said nucleic acid binding matrix,
wherein at least part of the target nucleic acid binds directly to the silica surface.

20. Method according to claim 19, wherein said hydrophobic group comprises a substituted or unsubstituted alkyl substituent having a length of from 1 to 50 C-atoms, wherein said alkyl substituent may have a branched or linear structure.

21. Method according to claim 19, wherein said nucleic acid binding matrix is contacted with a silane compound comprising the at least one hydrophobic group.

22. Method according to claim 21, wherein said nucleic acid binding matrix is provided with hydrophobic groups by contacting said matrix with at least one compound selected from the following groups of compounds:
reactive silane compounds comprising at least one hydrophobic group
monofunctional, bifunctional or trifunctional silane compounds comprising at least one hydrophobic group
alkoxysilane compounds, halosilane compounds or aminosilane compounds comprising at least one hydrophobic group, and

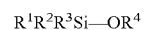

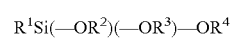

or $R^1R^2R^3Si—N(CH_3)_2$ $R^1R^2Si\,Me\text{-}(N(CH_3)_2$ $R^1Si\,Me_2\text{-}(N(CH_3)_2$ wherein $R^1$, $R^2$, $R^3$, and/or $R^4$ have the same or a different meaning and are independently selected from the group consisting of hydrogen, alkyl substituent, alkylene substituent and a functional group, and wherein at least one of $R^1$, $R^2$, $R^3$, and/or $R^4$ is an alkyl substituent having a length of 1 to 50 C-atoms which may be substituted or unsubstituted.

23. Method according to claim 22, wherein said at least one compound used for modifying said nucleic acid binding matrix with hydrophobic groups is selected from the group consisting of propyltriethoxysilane (PTS), octadecyltrimethoxysilane (OTM), hexadecyltrimethoxysilane (HMS), octyltrimethoxysilane (OTS), tetradecyltrimethoxysilane and octadecyltrimethoxysilane.

* * * * *